(12) United States Patent
Antonov

(10) Patent No.: US 11,369,712 B1
(45) Date of Patent: Jun. 28, 2022

(54) BAFFLES FOR MODIFYING AIRFLOW IN UV AIR STERILIZATION DEVICE

(71) Applicant: Evgeny Antonov, Staten Island, NY (US)

(72) Inventor: Evgeny Antonov, Staten Island, NY (US)

(*) Notice: Subject to any disclaimer, the term of this patent is extended or adjusted under 35 U.S.C. 154(b) by 0 days.

(21) Appl. No.: 17/156,734

(22) Filed: Jan. 25, 2021

(51) Int. Cl.
*A61L 9/20* (2006.01)

(52) U.S. Cl.
CPC ............. *A61L 9/20* (2013.01); *A61L 2209/12* (2013.01)

(58) Field of Classification Search
None
See application file for complete search history.

(56) References Cited

U.S. PATENT DOCUMENTS

| | | | |
|---|---|---|---|
| 6,855,295 B2 | 2/2005 | Kulp | |
| 7,332,124 B2* | 2/2008 | Trifu | F24F 8/192 422/4 |
| 8,038,949 B2 | 10/2011 | Horne et al. | |
| 8,481,985 B2 | 7/2013 | Neister | |
| 8,497,491 B2 | 7/2013 | Goldshtein et al. | |
| 8,541,758 B1* | 9/2013 | Filson, II | A61L 9/20 250/455.11 |
| 9,308,289 B2 | 4/2016 | Graff et al. | |
| 9,345,798 B2 | 5/2016 | Trapani | |
| 9,457,120 B2* | 10/2016 | Matsui | A61L 9/00 |
| 9,694,094 B1* | 7/2017 | Wedding | B01J 19/088 |
| 9,919,067 B2* | 3/2018 | Nevin | F04B 41/02 |
| 10,010,633 B2 | 7/2018 | Trapani | |
| 10,039,854 B2 | 8/2018 | Kirschman | |
| 10,220,110 B2 | 3/2019 | Kim et al. | |
| 10,328,174 B2 | 6/2019 | Jaworski et al. | |
| 10,532,122 B2 | 1/2020 | Kirschman | |
| 2006/0284109 A1* | 12/2006 | Scheir | A61L 9/20 250/455.11 |
| 2008/0121823 A1* | 5/2008 | Goel | A61L 9/20 250/504 R |

(Continued)

FOREIGN PATENT DOCUMENTS

| | | |
|---|---|---|
| WO | 2010/045668 A2 | 4/2010 |
| WO | 2011/031167 A1 | 3/2011 |
| WO | 2020/113149 A1 | 6/2020 |

OTHER PUBLICATIONS

Kront Co. (Latvia), "DEZAR—Breathe clean air free of bacteria and viruses in any room and any time," http://kront.eu/en/landing, checked Jan. 17, 2021.

(Continued)

*Primary Examiner* — Andrew Smyth
(74) *Attorney, Agent, or Firm* — Andrew Berks; Gallet Dreyer & Berkey LLP

(57) ABSTRACT

One or more air baffles are provided for an apparatus that sterilizes air in a room using UVC radiation. At least one baffle within an air sterilization enclosure is arranged so the baffle is proximal to the at least one UVC light source. The baffle is designed and positioned to create air turbulence within the enclosure to increase the dwell time of a given volume of the air in the enclosure, and to reduce the effective distance of a given volume of air to the UVC light sources. Thus, airflow is hindered by the baffle in its passage through the enclosure in order to increase the UVC exposure to that volume of air.

7 Claims, 7 Drawing Sheets

(56) References Cited

U.S. PATENT DOCUMENTS

| | | | | |
|---|---|---|---|---|
| 2008/0138241 A1* | 6/2008 | Naarup | ................... | A61L 9/015 422/4 |
| 2010/0254852 A1* | 10/2010 | Metteer | .................. | B01D 53/75 422/4 |
| 2014/0050612 A1* | 2/2014 | Kneissl | ..................... | A61L 2/10 250/435 |
| 2018/0021469 A1 | 1/2018 | Kim et al. | | |

OTHER PUBLICATIONS

Hiroko Inagaki , Akatsuki Saito , Hironobu Sugiyama , Tamaki Okabayashi & Shouichi Fujimoto (2020) Rapid inactivation of SARS-CoV-2 with deep-UV LED irradiation, Emerging Microbes & Infections, 9:1, 1744-1747, DOI: 10.1080/22221751.2020. 1796529.

Ariza-Mateos A, Prieto-Vega S, Diaz-Toledano R, Birk A, Szeto H, Mena I, Berzal-Herranz A, Gómez J. RNA self-cleavage activated by ultraviolet light-induced oxidation. Nucleic Acids Res. Feb. 2012;40(4):1748-66. doi: 10.1093/nar/gkr822. Epub Oct. 11, 2011. PMID: 21989404; PMCID: PM03287179.

Philips Lighting B.V., "Ultraviolet purification application information" https://www.assets.signify.com/is/content/PhilipsLighting/Assets/philips-lighting/global/20200504-philips-uv-purification-application-information.pdf, Checked Jan. 3, 2021.

Am. Soc. Heating, Refrigerating and Air-Conditioning Engineers, https://www.ashrae.org/File%20Library/About/Position%20Documents/Filtration-and-Air-Cleaning-PD.PDF (Sec. 2.4, pp. 10-11), checked Jan. 3, 2021.

Scott, K.J., Wills, R.B.H. and Patterson, B.D. Removal by ultraviolet lamp of ethylene and other hydrocarbons produced by bananas. J. Sci. Food Agric., 1971, 22: 496-497. https://doi.org/10.1002/jsfa.2740220916.

UV Resources, http://www.uvresources.com/blog/the-ultraviolet-germicidal-irradiation-uv-c-wavelength/ retrieved Dec. 30, 2020.

Oxidation TechnologiesfLLC, "Ozone production from UV," https://www.oxidationtech.com/ozone/ozone-production/uv-lamp.html retrieved Dec. 30, 2020.

American Ultraviolet®, "Upper Air Germicidal Solutions," https://www.americanultraviolet.com/documents/RAMcutSheet1_26.pdf (checked Jan. 18, 2021).

Larsen Electronics LLC, "UV Air Sanitation Purifier," https://www.larsonelectronics.com/product/269249/uv-air-sanitation-purifier-120v-2-60w-t8-uvc-lamps-15-16-3-soow-cord-occupied-areas (downloaded Jul. 31, 2020).

Bianco A, M Biasin, G Pareschi et al, UV-C irradiation is highly effective in inactivating and inhibiting SARS-CoV-2 replication. medRxiv, publ Jun. 7, 2020 https://doi.org/10.1101/2020.06.05.20123463.

Christiane Silke Heilingloh, Susceptibility of SARS-CoV-2 to UV irradiation, Am J. Inf Control, 2020, 48(10), p. 1273-1275, published Aug. 4, 2020, https://doi.org/10.1016/j.ajic.2020.07.031.

Yoram Gerchman et al., UV-LED disinfection of Coronavirus: Wavelength effect, J Photochem and Photobiol. B: Biology, 2020, 212, 112044, https://doi.org/10.1016/j.jphotobiol.2020.112044.

Data sheet: https://www.assets.lighting.philips.com/is/content/PhilipsLighting/fp928039004005-pss-en_ae.

Larsen Electronics LLC, "150W In-duct UVC Disinfection Light," https://www.larsonelectronics.com/product/269257/150w-in-duct-uvc-disinfection-light-120-277v-360-coverage-low-maintenance (downloaded Jul. 31, 2020).

* cited by examiner

BAFFLES FOR MODIFYING AIRFLOW IN UV AIR STERILIZATION DEVICE

FIELD OF THE INVENTION

This invention is directed to devices that affect the airflow in air sterilization equipment operating in the ultraviolet C (UVC) wavelengths.

BACKGROUND

The use of ultraviolet (UV) radiation is well known as a means to sterilize air and materials. By the term "sterilize," it is meant that microorganisms, such as bacteria, fungi, and viruses, are killed or deactivated so as to be unable to reproduce. UV radiation sterilizes microorganisms by damaging nucleic acids and disrupting their DNA and RNA,[1] leaving them unable to perform vital functions. UV germicidal irradiation is used in a variety of applications, including food, air, and water purification. UV germicidal irradiation may have the advantage that heat and exposure to harsh chemicals are avoided, and the radiation itself is transient. As used herein, the term "disinfect" is synonymous with "sterilize," and the term "germicidal" is synonymous with "sterilizing."

[1] Ariza-Mateos A, Prieto-Vega S, Diaz-Toledano R, Birk A, Szeto H, Mena I, Berzal-Herranz A, Gomez J. RNA self-cleavage activated by ultraviolet light-induced oxidation. Nucleic Acids Res. 2012 February; 40(4):1748-66. doi: 10.1093/nar/gkr822. Epub 2011 Oct. 11. PMID: 21989404; PMCID: PMC3287179.

UV light conventionally is divided into several bands with wavelengths from 10 nanometers (nm) to 400 nm. UVA is 315 nm to 400 nm, UVB is 280 nm to 315 nm, and UVC is 100 nm to 280 nm.[2] Shorter wavelengths are termed "extreme" or "vacuum" ultraviolet and are strongly absorbed by the atmosphere.

[2] These bands are defined in ISO standard 21348.(2007)

This invention pertaining to UV sterilization employs UVC wavelengths. UV wavelengths around 265 nm, in the UVC band, is the optimal biocide wavelength to damage nucleic acids which can kill microorganisms. Thymine (and Uracil), components of DNA and RNA, have absorption spectra that are especially sensitive at wavelengths at or near 265 nm. At wavelengths longer than 300 nanometers, there is almost no absorption by nucleic acids. The absorbed energy can result in defects including pyrimidine dimers. These dimers can prevent replication or can prevent the expression of necessary proteins, resulting in the death or inactivation of the microorganism.[3]

[3] Philips Lighting B.V., "Ultraviolet purification application Information" https://www.assets.signify.com/is/content/PhiliosLighting/Assets/philips-li-ahtina/aloDal/20200504-philips-uv-purification-application-information.pdf, Checked Jan. 3, 2021

UVC light is weak at the Earth's surface because the ozone layer of the upper atmosphere blocks it. But within enclosed spaces in UVC sterilization equipment, strong enough UVC light can be produced in circulating air or water systems to kill microorganisms such as bacteria, viruses, molds, and other pathogens. The application of UV germicidal irradiation to disinfection has been an accepted practice since the mid-20th century. It has been used primarily in medical sanitation and sterile work facilities. Increasingly, it has been employed to sterilize drinking and wastewater since the holding facilities are enclosed and can be circulated to ensure a higher exposure to the UV radiation.

UV sterilization has also found renewed application in air purifiers. In laboratory studies, UVC has been effective in removing bacterial, fungi, viral and other pathogen aerosols. To this end, UVC for upper air, in-duct, and in-room systems was named by the American Society of Heating, Refrigerating and Air-Conditioning Engineers (ASHRAE) 2014 Position Document on Airborne Infectious Diseases as among the two highest research priorities for developing engineering control to reduce infectious disease transmission.[4] This has taken on a new urgency in the era of the Covid-19 pandemic.

[4] Am. Soc. Heating, Refrigerating and Air-Conditioning Engineers, https://www.ashrae.org/File %20Library/About/Position %20Documents/Filtration-and-Air-Cleaning-PD.PDF (Sec. 2.4, pp. 10-11), checked Jan. 3, 2021.

UVC light sources can also purify and remove chemical contaminants from air. UV lamps radiating at 254 nm may remove low concentrations of gaseous contaminants in air such as hydrocarbons and carbon monoxide.[5] UV light in the 240-315 nm range has been reported to decompose ozone.[6]

[5] Scott, K. J., Wills, R. B. H. and Patterson, B. D. Removal by ultra-violet lamp of ethylene and other hydrocarbons produced by bananas. J. Sci. Food Agric., 1971, 22: 496-497. https://doi.org/10.1002/jsfa.2740220916
[6] UV Resources, http://www.uvresources.com/blog/the-ultraviolet-germicidal-irradiation-uv-c-wavelength/ retrieved Dec. 30, 2020

UVC is blocked by many materials and is absorbed by the atmosphere. UV light sources require the use of fused quartz glass or other specialized glass materials that transmit UV. Conventional glass and most plastics are highly absorbent of UVC.

An additional feature of UVC is that wavelengths below about 240 nm generate ozone.[7] This is undesirable. Ozone has been shown to affect the respiratory, cardiovascular and central nervous system. Early death and problems in reproductive health and development are also shown to be associated with ozone exposure. Accordingly, most UV sterilization equipment is adapted to block wavelengths that produce ozone. In particular, low pressure mercury lamps have an emission band at 185 nm that can cause ozone formation, however, commercially available mercury lamps have materials or coatings that block this 185 nm band to prevent ozone formation by UV sterilization equipment.

[7] Oxidation Technologies, LLC, "Ozone production from UV," https://www.oxidationtech.com/ozone/ozone-production/uv-lamp.html retrieved Dec. 30, 2020

Direct exposure of people and pets to UVC is potentially harmful. The same mechanisms that kill microorganisms can harm people or animals. Humans may be susceptible to DNA damage from UVC, even though UVC is blocked by the skin, including outer layers of the skin, and UVC does not penetrate to the interior of the eye. Even so, UVC exposure to people can cause erythema (reddening of the skin), sunburn, and lead to skin cancer. Eye conditions include conjunctivitis (inflammation of the mucous membranes of the eye), photokeratitis and can lead to cataracts, pterygium and pinguecula formation. Because of this, when germicidal UV equipment is used, it is important to design systems to exclude UVC leakage and exposure of UV radiation to surrounding persons and pets to avoid these effects.

Light-emitting diode (LED) lights are available that produce UVC output at 265-270 nm suitable for UV sterilization devices. Another efficient light source for generating UVC is the low-pressure mercury discharge lamp, where on average 35% of input watts is converted to UVC watts. The radiation is generated almost exclusively at 254 nm which at about 85% of the maximum germicidal effect. Philips tubular UV (TUV) lamps have an envelope of special glass transparent to UV at 254 nm but that filters out ozone-forming radiation, in this case the 185 nm mercury line.

Several UV devices are available that can sterilize room air in occupied rooms. For example, American Ultraviolet® RAM Series in-room air treatment fixtures are designed specifically for upper air irradiation inside occupied rooms.[8] Another example is Larson Electronics® UV Air Sanitation Purifier.[9] Another example are the "Dezar" series of devices which include wall mounted and floor mounted devices in various sizes.[10] All of these devices use low pressure mercury TUV lamps.

[8] American Ultraviolet®, "Upper Air Germicidal Solutions," https://www.americanultraviolet.com/documents/RAMcutSheet1_26.pdf (checked Jan. 18, 2021)
[9] Larsen Electronics LLC, "UV Air Sanitation Purifier," https://www.larson-electronics.com/product/269249/uv-air-sanitation-purifier-120v-2-60w-t8-uvc-lamps-15-16-3-soow-cord-occupied-areas (downloaded Jul. 31, 2020)
[10] Kront Co. (Latvia), "DEZAR—Breathe clean air free of bacteria and viruses in any room and any time," http://kront.eu/en/landing, checked Jan. 17, 2021

Recent papers have reported that SARS-CoV-2, the causative agent of Covid-19, is susceptible to UV radiation, at 254 nm,[11,12] at 280 nm,[13] and 267 nm (3-log inactivation at irradiation 6-7 mJ/cm$^2$).[14] Thus, there is considerable urgency in developing improved methods for disinfecting air. Given the known transmission of SARS-CoV-2 through droplets in air,[11] disinfecting room air may be critically important.

[11] Bianco A, M Biasin, G Pareschi et al, UV-C irradiation is highly effective in inactivating and inhibiting SARS-CoV-2 replication. medRxiv, publ Jun. 7, 2020 https://doi.org/10.1101/2020.06.05.20123463
[12] Christiane Silke Heilingloh, Susceptibility of SARS-CoV-2 to UV irradiation, Am J. Inf Control, 2020, 48(10), P1273-1275, published Aug. 4, 2020, https://doi.org/10.1016/j.ajic.2020.07.031
[13] Hiroko Inagaki, et al. Rapid inactivation of SARS-CoV-2 with deep-UV LED irradiation, Emerging Microbes & Infections, (2020) 9:1, 1744-1747, DOI: 10.1080/22221751.2020.1796529
[14] Yoram Gerchman et al., UV-LED disinfection of Coronavirus: Wavelength effect, J Photochem and Photobiol. B: Biology, 2020, 212, 112044, https://doi.org/10.1016/j.jphotobiol.2020.112044

SUMMARY OF THE INVENTION

This invention provides an air baffle for an apparatus for sterilizing air in a room using UVC radiation. Such are sterilization devices are available, having an enclosure with at least one fan for circulating room air through the enclosure and at least one UVC light source within the enclosure. Of particular value are UVC air sterilization enclosures that can be used in occupied rooms. Such enclosures for occupied rooms need to shield the UVC radiation so that air circulated through the enclosure is disinfected by UVC radiation, but the UVC radiation is completely enclosed so as not to leak out and harm people, pets, or equipment (that may be UV sensitive) in the room. At least one baffle within the enclosure is provided, arranged so the baffle is proximal to the at least one UVC light source. The baffle is designed and arranged so that it creates air turbulence within the enclosure to Increase the dwell time of a given volume of the air in the enclosure. Thus, a given volume of air is hindered by the baffle in its passage through the enclosure in order to increase the UVC exposure to that volume of air. This is expected to increase the efficiency of sterilization of air flowing through the apparatus.

In an embodiment, the baffle may have a central post having at least two surfaces oriented at vertically opposite angles with respect to a vertex comprising an axis perpendicular to a longitudinal axis of the post.

In an embodiment, the baffle may have two or more parallel surfaces on each side of the post, wherein the parallel surfaces on each side of the post are oriented at vertically opposite angles with respect to a vertex comprising an axis perpendicular to a longitudinal axis of the post, and each such vertex and surfaces at vertically opposite angles comprise a set, and wherein there is a vertex for each set of parallel surfaces.

In an embodiment, the apparatus and baffle may include a clip that supports a tubular UV lamp.

In an embodiment, the apparatus and baffle may further include baffles oriented in more than one direction around a cross section of a tubular UV lamp.

In an embodiment, the UVC light source is a tubular low-pressure mercury lamp with an emission primarily at 254 nm. In an embodiment, the UVC light source is a light emitting diode (LED) tuned to emit light at 240-285 nm, preferably at 265 nm±10 nm.

DESCRIPTION OF THE DRAWINGS

FIG. 5A is a top view plan of the interior components of the main body section. FIG. 5B is a cross-section view through line M-M' in FIG. 5A. FIG. 5C is a side elevation of the main body section of a representative air sterilization apparatus. FIG. 5D is a side elevation a representative air sterilization apparatus with the cover section in position. FIG. 5E is an elevation view of the bottom of a representative air sterilization apparatus. FIG. 5F is an elevation view of the top of a representative air sterilization apparatus.

DETAILED DESCRIPTION

Figure 1A:
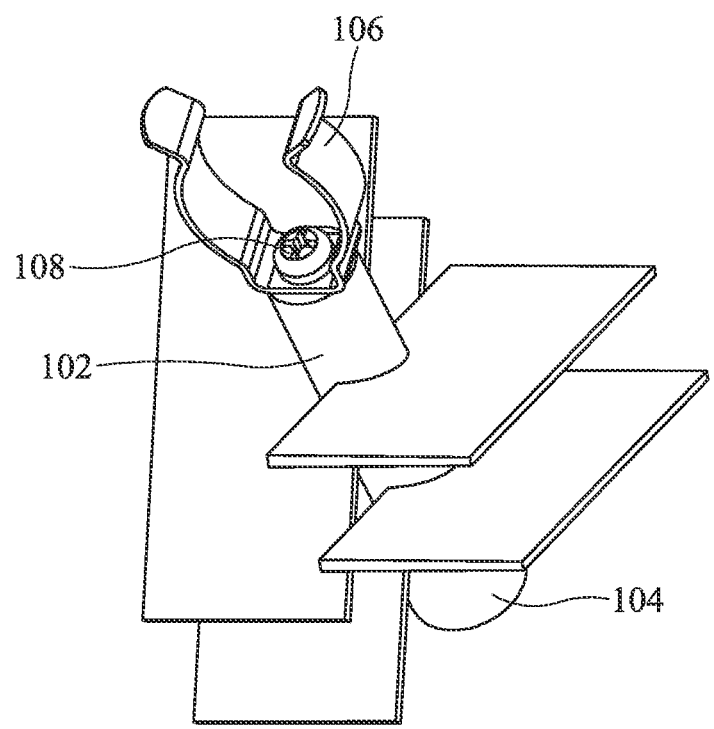
FIG. 1A is a perspective of the inventive baffle.

In air and surface disinfection applications the UV effectiveness is estimated by calculating the UV dose which will be delivered to the microbial population. The UV dose is calculated in eq. 1:

$$\text{UV dose } (\mu W \cdot s/cm^2) = \text{UV intensity } (\mu W/cm^2) \times \text{exposure time (seconds)} \quad \text{(eq. 1)}$$

The UV intensity is specified for each lamp at a distance of 1 meter. UV intensity is inversely proportional to the square of the distance, so it decreases at longer distances. Alternatively, it rapidly increases at distances shorter than 1 m. Additionally, increasing exposure time proportionally increases the UV dose.

In the air purification apparatus disclosed herein, the UV dose is the dose of radiation that a volume of air is exposed to in the interior of a chamber (205) containing UVC light sources for sterilizing air. In static applications the exposure time can be as long as needed for an effective UV dose to be reached. In case of rapidly moving air, such as in air ducts or wall mounted recirculating air purification systems, the exposure time is short, so a sufficient UV intensity can be achieved by using higher power UV lamps, or multiple UV lamps. In this invention, baffles are disclosed to increase air turbulence inside recirculating air purification devices to disrupt a smooth air flow and keep any particular volume of air exposed to the radiation sources for more time, and concomitantly reduce the effective distance between a given volume of air and the light sources, thereby increasing the effective UV dose, and the sterilization efficiency of the air purification device.

An optimum radiation wavelength for killing microorganisms such as bacteria, fungi, and viruses has been reported to be about 265±10 nM.[3,14] LED UVC light sources are capable of producing UVC at this wavelength, but from eq. 1 it is clear that intensity expressed in watts per unit area are proportional to the dose required to kill microorganisms, and LED UVC lamps tend to be expensive in terms of power (watts) per unit area as comparted to low pressure mercury lamps. By contrast to LED's, low pressure mercury lamps such as a Philips® TUV T8 25 W lamp produce much higher power and may be more cost effective. The mercury emission line is at 254 nm, and while slightly off optimum, is still highly effective at killing microorganisms. Several manufacturers make low pressure mercury lamps in a variety of output powers that can be used in air purification equipment. The inventive baffles can be installed in such air purification equipment to increase the dwell time that a given volume of air is exposed to the UVC radiation.

By the term "volume of air," an arbitrary hypothetical volume of air is meant, for example one mL of air. Any particular mL of air circulated through an air purification apparatus is hindered in its passage through the apparatus by the invention herein. Thus, such a volume of air is exposed for a longer time to the UVC radiation, thereby increasing the effectiveness of the UVC radiation at killing any microorganisms or viral particles suspended in the air.

In an embodiment, this invention provides an air baffle for an apparatus for sterilizing air in a room. The baffle creates air turbulence within the enclosure to increase the dwell time of a given volume of the air in the enclosure. The discussion below pertains to a representative apparatus that sterilizes air in an occupied room. Other air sterilization devices are possible, but this is a representative example.

An embodiment of a baffle according to this invention is shown in FIGS. 1A-1D. FIG. 1A is a perspective of the top of a baffle 100. This embodiment has two sets of parallel surfaces on each side of a central post 102. The post may have a clip 106 on top that can grasp or support a tubular low-pressure mercury UV lamp, for example a Philips® TUV T8 25 W.[15] The clip 106 may be secured to the post with screw 108. The post also has a base section 104 that may be secured to an enclosure. In an embodiment, the clips support a UV lamp in an enclosure. In an embodiment, the lamp is supported by other means and the clip secures the baffle to the lamp.

[15] Data sheet: Philips Lighting, "TUV 25 W 1SL/25 Data Sheet," https://www.assets.lighting.philips.com/is/content/PhilipsLighting/fp928039004005-pss-en_ae (checked Jan. 22, 2021)

In the embodiment in FIGS. 1A-1D, the parallel surfaces form two sets, with one surface from each set on each side of the central post, and the two surfaces in each set are oriented at vertically opposite angles at approx. 50° on an arc from each surface to a longitudinal line through the post. The surfaces in FIGS. 1A-1D are denoted 110, 112, 114, and 116. The vertically opposite angles are visualized in FIG. 1D. Thus, in the view shown in FIG. 1D, surfaces 110 and 114 are vertically opposite, and surfaces 112 and 116 are vertically opposite.

Figure 1B:
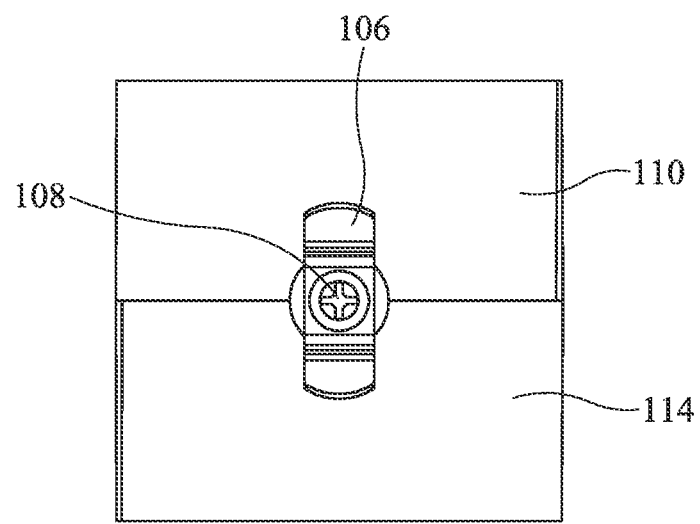
FIG. 1B is an elevation view of the top of an embodiment of the inventive baffle.
Figure 1C:
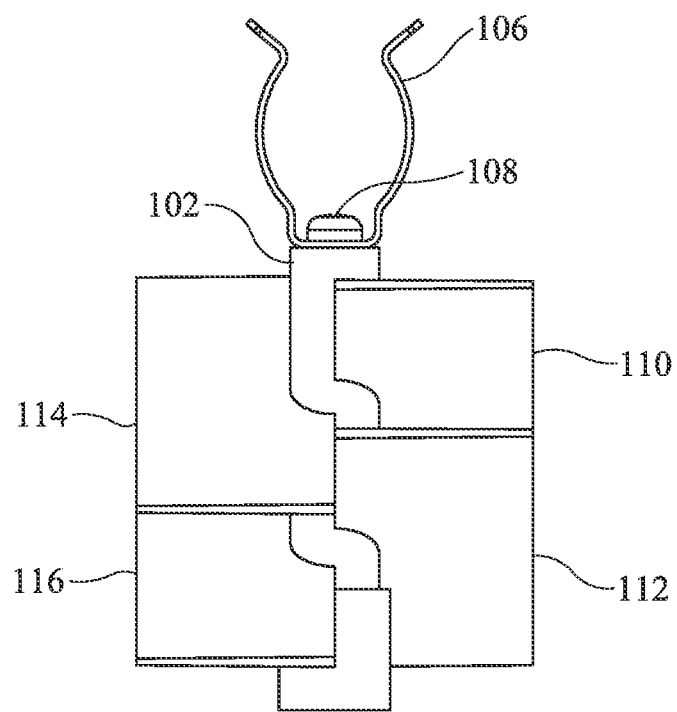
FIG. 1C is an elevation view of the front of an embodiment of the inventive baffle showing the face of each surface.
Figure 1D:
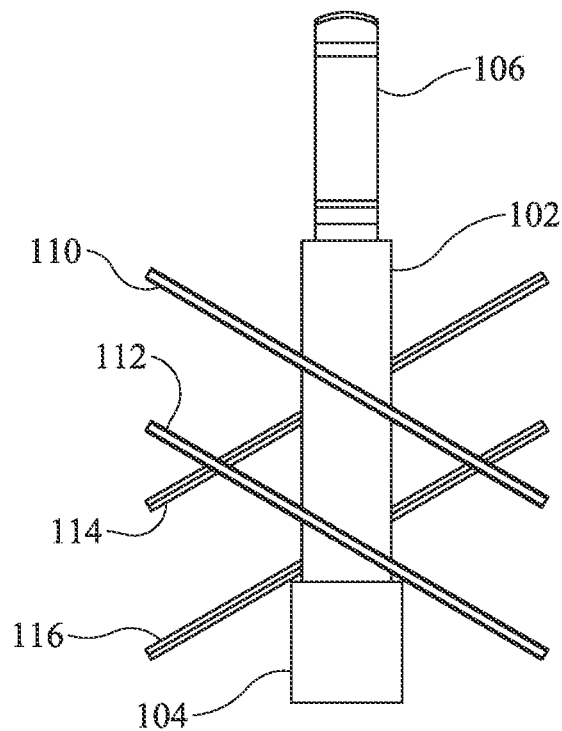
FIG. 1D is an elevation view of the side of an embodiment of the inventive baffle showing side views of each baffle surface.

FIG. 1B is a top-down view of the embodiment in FIG. 1A. FIG. 1C is a front elevation. FIG. 1D is a side elevation. This arrangement of surfaces is intended to create air turbulence around UV light tubes (or another UV light source) in an enclosure for purifying air.

In an embodiment, a baffle has a central post having at least two surfaces oriented at vertically opposite angles with respect to a vertex comprising an axis perpendicular to a longitudinal axis of the post.

"Vertically opposite angles" is a term in Euclidian geometry, meaning a pair of equal angles between a pair of intersecting lines.

In an embodiment, two or more parallel surfaces are provided on each side of the post, wherein the parallel surfaces on each side of the post are oriented at vertically opposite angles with respect to a vertex comprising an axis perpendicular to a longitudinal axis of the post, and each such vertex and surfaces at vertically opposite angles comprise a set, and wherein there is a vertex for each set of parallel surfaces.

Figure 2A:
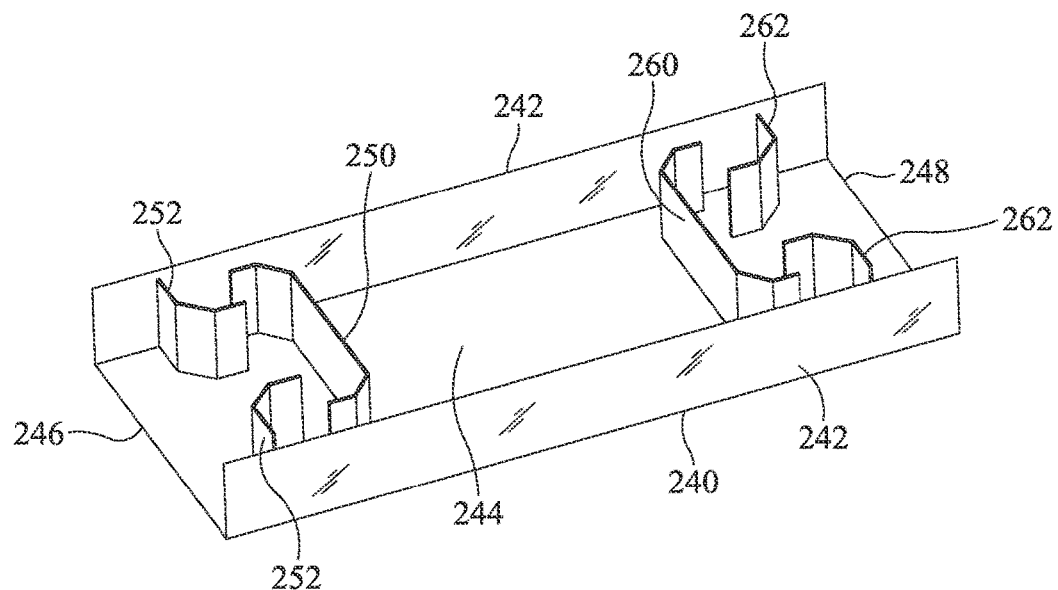
FIGS. 2A and 2B are perspective views depicting a cover section (FIG. 2A) and main body (FIG. 2B) of a representative air sterilization apparatus having six inventive baffles installed therein.
Figure 2B:
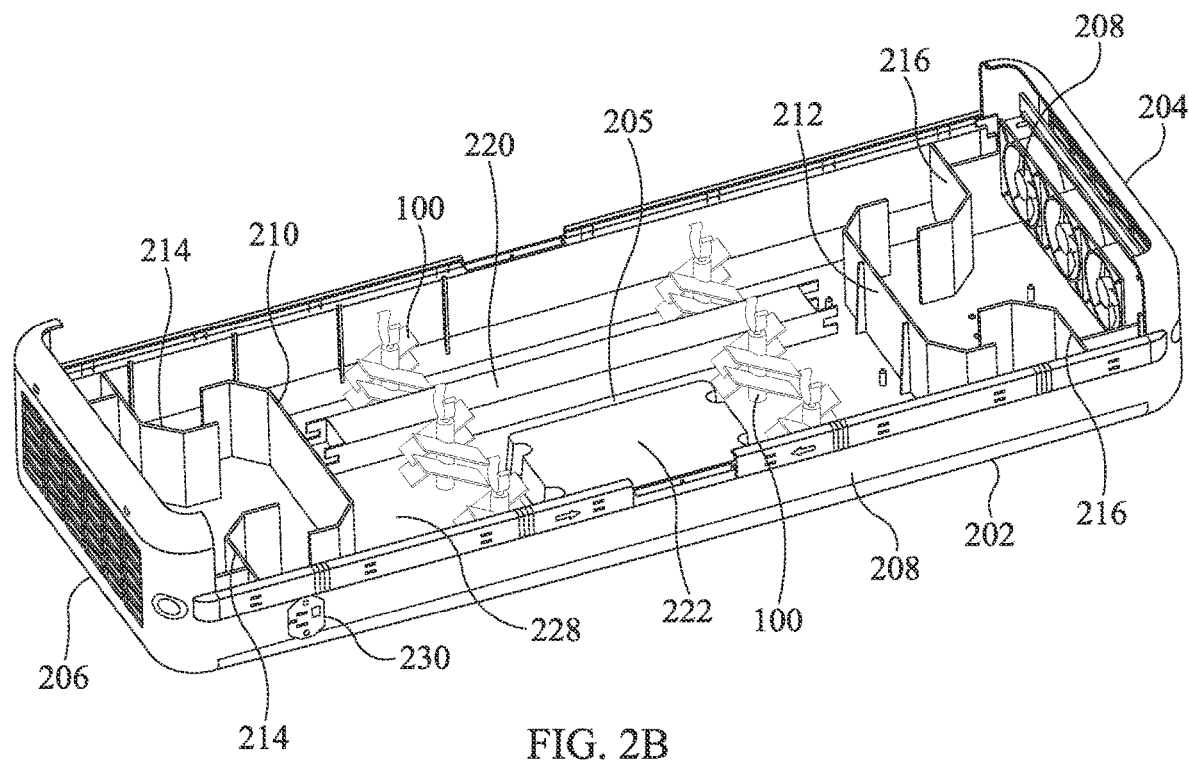
Figure 3:
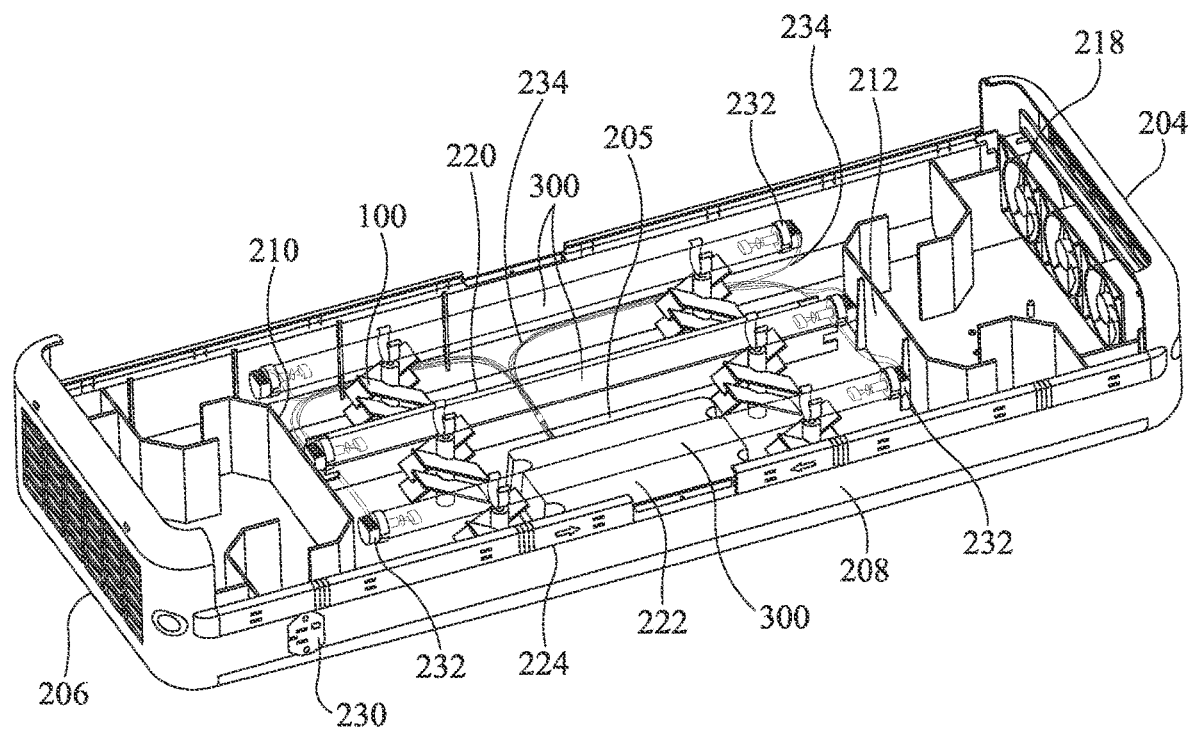
FIG. 3 is a perspective view of a representative air sterilization apparatus having six inventive baffles installed therein and also showing three tubular UVC low pressure mercury lamps.

In an embodiment, an exemplary air purification apparatus 200 is shown in FIGS. 2-8. FIGS. 2A and 2B show the cover and main body respectively of the exemplary apparatus. The light tubes are omitted in FIG. 2B but are shown in FIG. 3. This type of apparatus is meant to operate in an occupied room. Accordingly, the UV light must be shielded and prevented from leaking out. With respect to exemplary air purification apparatus 200, 204 is denoted as the "top" and 206 is denoted as the "bottom" of the apparatus. The cover 240 is denoted the "front" of the apparatus, and the exterior surface 229 of the panel in the main body is denoted the "back" of the apparatus.

The interior surfaces of the enclosure may be reflective and coated with a gold or aluminized coating that is highly reflective to UV radiation.[3] Additionally, the baffles 210, 212, 214, and 216 shield the UV light from the external environment and may be coated with a UV absorptive material. In an embodiment, the surfaces 110, 112, 114, and 116 in the inventive baffles may be coated with a UV reflective material in order to increase the exposure of moving air inside the enclosure to biocidal UV radiation.

In FIG. 2B, the main body 202 includes the electrical components and supports for the light tubes. As shown, baffles 210, 212, 214, and 216 shield the UV light from the external environment and provide a circuitous path for air currents (FIG. 8) that improves the performance of the apparatus. In an embodiment, end 204 is denoted the "top" and 206 is denoted the "bottom" of a representative apparatus. Top end 204 has one or more fans 218 embedded therein, that draw outside air from bottom end 206 and forces the air out top end 204. As shown in FIGS. 2-8, there are three fans.

Figure 4:
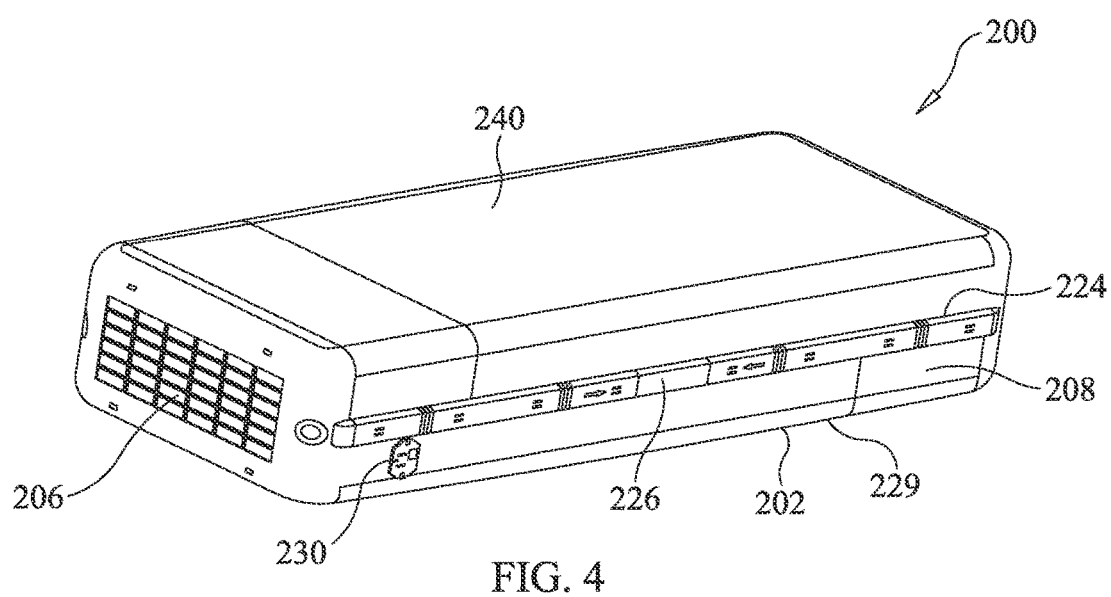
FIG. 4 is a perspective view of the exterior of a representative air sterilization apparatus with the cover in place.

FIG. 2A is the top cover 240 that fits over the enclosure body 202. When the top cover 240 is mated with main body 202, cover 240 is flipped over. The complete enclosure with top cover 240 in place is shown in FIGS. 4 and 5D. FIG. 2A shows the interior face of the top cover. The interior surface in FIG. 2A is 244. End 248 fits over end 204 and end 246 fits over end 206 in the enclosure body. The cover 240 includes baffles 250, 252, 260, and 262 that match baffles 210-216 in the enclosure body. Thus, baffle 250 joins baffle 210, baffles 252 (two) join baffles 214, baffle 260 joins baffle 212, and baffles 262 (two) join baffles 216. The connection of the baffles from the cover and enclosure body is important, because these baffles prevent UVC radiation from escaping from the enclosure. Top cover walls 242 mate with walls 208 in the enclosure body. In an embodiment, a band 224 forms a union between walls 242 and walls 208, to help ensure that interior radiation does not escape. Latch 226 is used to secure cover 240 to body 202.

Light tubes 300 are depicted in FIG. 3 in place in the chamber 205 in the enclosure body. In the exemplary embodiment, conventional tubular mercury low-pressure lamps are used, for example a Philips® TUV T8 25 W lamp. Other UV lamps are also within the scope of this invention; germicidal mercury lamps are available ranging in size from 4 watts to 800 watts. Some of these lamp styles are tubular as illustrated in the examples herein. Other lamp styles are within the scope of this invention, providing baffles that create air turbulence in a chamber equivalent to 205 having UVC lamps for sterilizing air. That is, the inventive baffles decrease the distance between a given volume of air and the UV light sources, and to increase the dwell time of a given volume of air within the chamber. At this time, these mercury lamps are more cost effective than LED light sources, with a much lower UV-power to cost ratio, but LED light sources may also be workable in this or similar apparatus. The tubes 300 as depicted are supported by posts 102 and clips 106. In this embodiment, two supports are provided for each UV light tube. Each tube as a cap base 232 at each end of the tube. Typically, UVC lamps have a two-pin electrical connection at each end, and the cap base fits over these connections. These types of tubes are a fluorescent-type of lamp, and therefore require a ballast, shown in enclosure 220 affixed to back panel 228 of the main body 202 (FIG. 2B). Wires 234 (FIG. 3) lead from each cap base to ballast enclosure 220. Also depicted in FIG. 2B is an enclosure 220 for other electrical apparatus for the entire enclosure, such as power supply to the ballast, power for the fans, on/off controls, and other conventional electrical control equipment.

In an alternative embodiment, for example with LED light sources, one or more baffles may be arranged within a chamber 205 designed to create air turbulence in accordance with the invention, to decrease the distance between a given volume of air and the UV light sources, and to increase the dwell time of a given volume of air within the chamber. Both of these factors will result in an increased UV dose the volume of air is exposed to, in accordance with eq. 1.

Figure 5A:
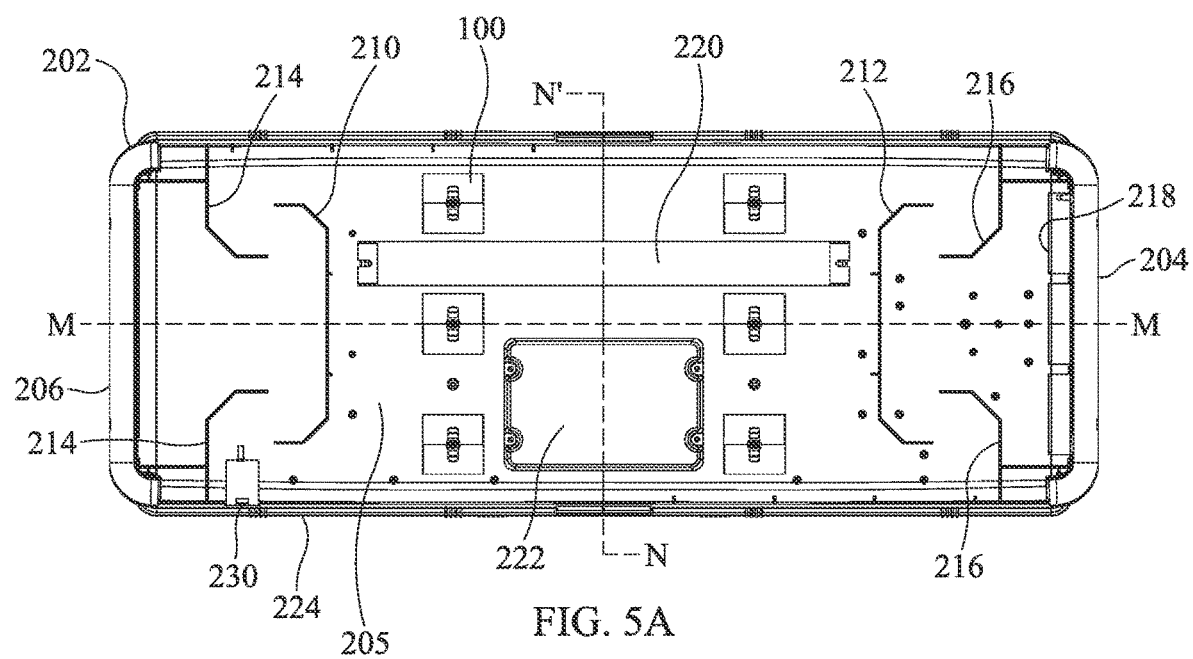
FIGS. 5A-5F are plan drawings of a representative air sterilization apparatus.
Figure 5B:
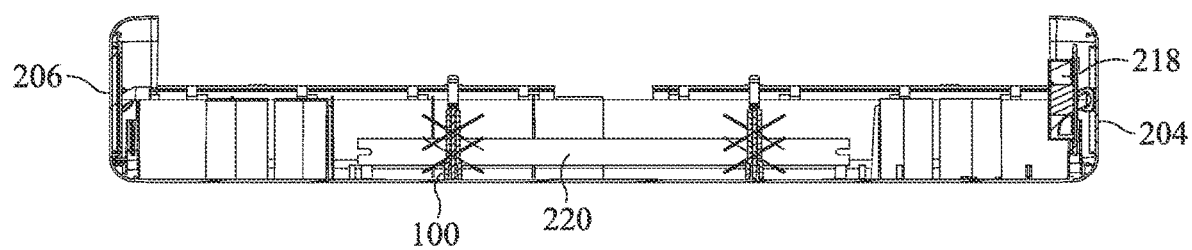
Figure 5C:
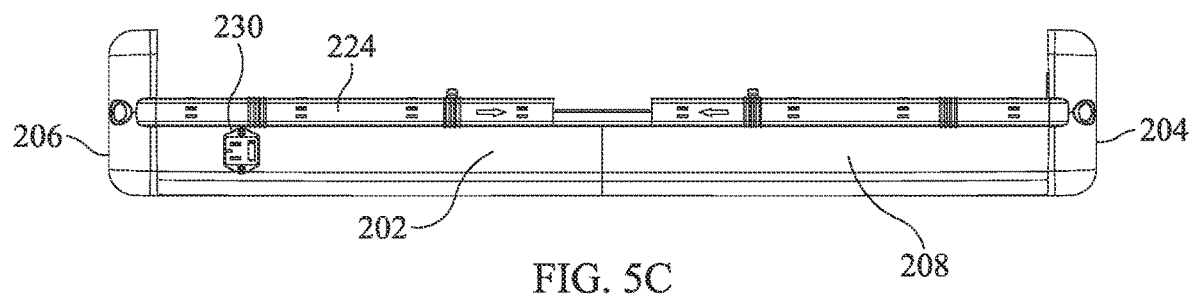
Figure 5D:
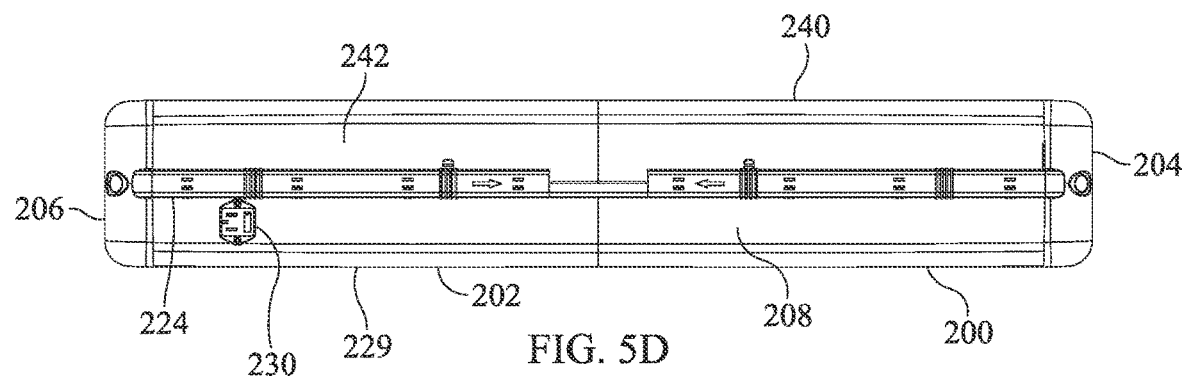
Figure 5E:
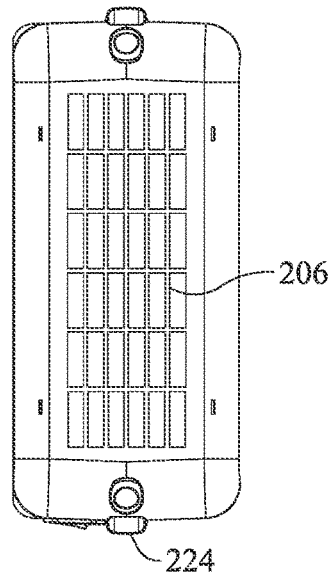
Figure 5F:
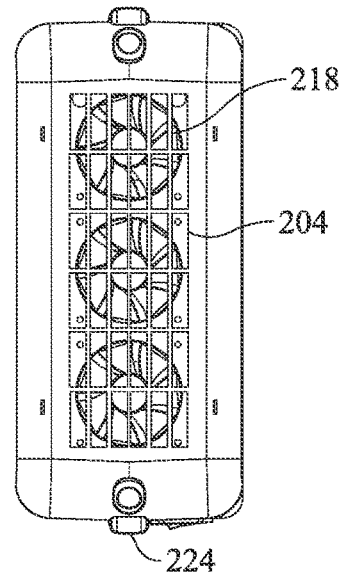

FIGS. 5A-5F show further views of the enclosure. FIG. 5A is a top elevation view of the main body 202 of the enclosure. FIG. 5B is a cross section through line M-M' in FIG. 5A. FIG. 5C is an external side elevation view of the main enclosure body 202 without the top in place. FIG. 5D is an external side elevation view of the apparatus 200, showing the top 240 mated with main body 202. FIG. 5E shows an elevation view of the bottom end 206, FIG. 5F shows an elevation view of the top end 204.

Figure 6:
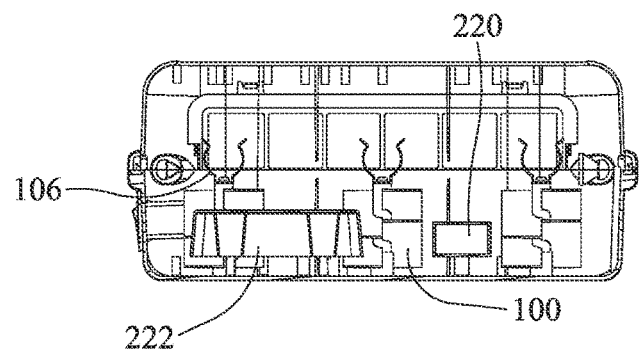
FIG. 6 is a cross section view of a representative air sterilization apparatus through line N-N' in FIG. 5A.

FIG. 6 is a latitudinal cross section through line N-N' in FIG. 5A, of the complete apparatus showing the top mated to the bottom, and clips 106 that would support UVC light tubes 300.

Figure 7:
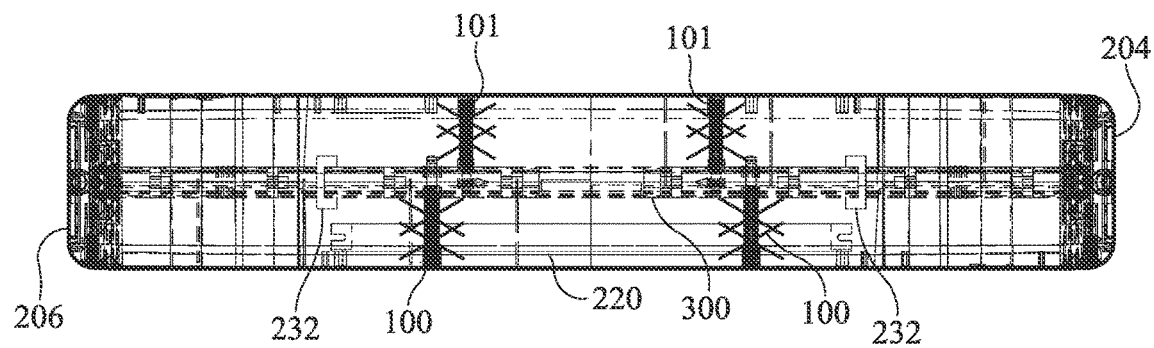
FIG. 7 is a cross-section view through line M-M' in FIG. 5A of an alternative embodiment showing baffles 100 in front of and behind tube 300.

FIG. 7 is an alternative embodiment showing an additional set of baffles 101 mounted on the interior surface 244 of cover 240, to increase the air turbulence inside the main chamber 205 of the enclosure. Additional baffles can be used in this invention, to create a circuitous air path within an enclosure to increase the exposure of any given volume of air to UVC radiation within chamber 205.

Figure 8:
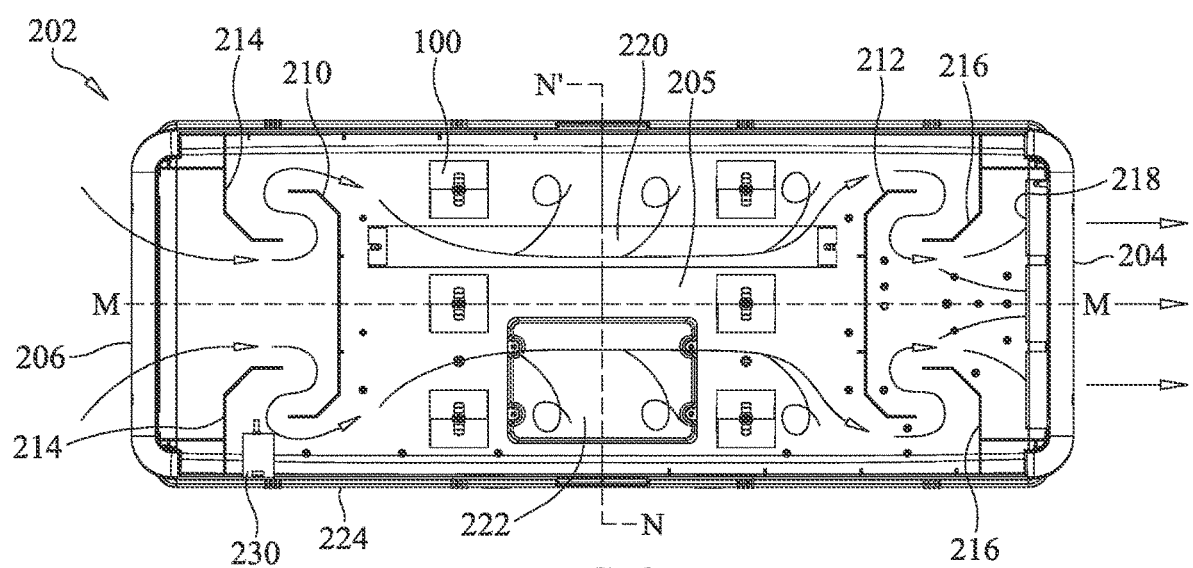
FIG. 8 is the plan view of FIG. 5A showing air flow through a representative air sterilization apparatus with baffles 100 in place.

FIG. 8 is shows air flow, depicted with arrows, in an exemplary enclosure. Air is drawn in from a grille at end 206, conventionally referred to as the "bottom end" in this disclosure. The air flow encounters baffles 214 and 210, and then enters chamber 205 having three UVC light tubes (in this embodiment). The air is drawn upward from fans 218 that pull the air flow through chamber 205, past baffles 212 and 216, and out end 204.

Baffles 210 to 216 have a two-fold purpose of blocking the escape of UVC radiation from either end of the enclosure, and also to create turbulence in the interior of the enclosure. The inventive baffles 100 are expected to considerably increase air turbulence inside the enclosure as shown by the air flow arrows in FIG. 8. Because the UV dose is proportional to time of radiation exposure and proportional to the square of the distance between UVC light sources and a given volume of air, by increasing the turbulence in the enclosure, any given volume of air is deflected and forced into closer proximity to the UVC lamps, and air flow is slowed down and exposed for a longer period to the UVC radiation in the interior 205 of the apparatus. These effects are expected to increase the germicidal efficiency of UVC air purification devices that recirculate room air through the purification device.

Alterative devices besides those depicted in FIG. 2-8 are within the scope of this invention. For example, the inventive baffles may be of value in other designs of in-use room air purifiers such as those from American Ultraviolet®[8] and Larson Electronics®.[9] UVC air purification devices are also available for installation in ductwork.[16] All of these designs rely on UVC light tubes, and the inventive baffles can be installed inside these units to increase turbulence and exposure time (dwell time) of a given volume of air to the UVC radiation, and increase the biocidal radiation dose to increase the effectiveness of these devices.

[16] Larsen Electronics LLC, "150 W In-duct UVC Disinfection Light," https://www.larsonelectronics.com/product/269257/150w-in-duct-uvc-disinfection-light-120-277v-360-coverage-low-maintenance (downloaded Jul. 31, 2020).

| DRAWING LEGEND | |
| --- | --- |
| Number | Description |
| 100 | Baffle unit with clip and 4 baffle surfaces |
| 101 | Additional baffles mounted on cover. |
| 102 | Baffle unit post |
| 104 | Post base section |
| 106 | Clip for supporting UV light tube |
| 108 | Screw securing clip to baffle unit post |
| 110 | Baffle surface |
| 112 | Baffle surface |
| 114 | Baffle surface |
| 116 | Baffle surface |
| 200 | Exemplary enclosure |
| 202 | Main body of exemplary enclosure |
| 204 | Top end of exemplary enclosure |
| 205 | Interior chamber of enclosure with UVC lamps |
| 206 | Bottom end of enclosure |
| 208 | Side wall of main body (2) |
| 210 | Baffle at bottom portion of enclosure |
| 212 | Baffle at top portion of enclosure |
| 214 | Secondary baffle (2) |
| 216 | Secondary top baffle (2) |
| 218 | Fans at top of exemplary enclosure main body |
| 220 | Housing for ballast in main body of enclosure |
| 222 | Electrical housing in main body of enclosure |
| 224 | Band at junction of main body and cover |

-continued

DRAWING LEGEND

| Number | Description |
|---|---|
| 226 | Latch for detaching cover from main body |
| 228 | Interior surface of back panel of main body |
| 229 | Exterior surface of back of main body |
| 230 | External electrical connector |
| 232 | Cap base for lamp (6) |
| 234 | Wires from cap base to ballast |
| 240 | Enclosure cover section - front side |
| 242 | Cover section side wall |
| 244 | Interior surface of cover 240 |
| 246 | Edge of cover section at bottom end |
| 248 | Edge of cover section at top end. |
| 250 | Baffle at bottom end of cover section |
| 252 | Secondary baffle (2) at bottom end of cover section |
| 260 | Baffle at top end of cover section |
| 262 | Secondary baffle (2) at top end of cover section |
| 300 | Low Pressure Mercury UV lamp, Philips ® TUV T8 25 W |

The invention claimed is:

1. An air baffle for an apparatus for sterilizing air in a room, the apparatus having an enclosure with at least one fan for circulating room air through the enclosure and at least one UVC light source within the enclosure, such that the enclosure shields the room from UVC radiation, comprising at least one baffle within the enclosure and proximal to the at least one light source, wherein the baffle creates air turbulence within the enclosure to increase the dwell time of a given volume of the air in the enclosures;

wherein the baffle comprises a central post having at least two planar parallel surfaces oriented at vertically opposite angles with respect to a vertex comprising an axis perpendicular to a longitudinal axis of the post; and wherein the planar parallel surfaces are adjacent the central post and each planar surface extends past the vertex's axis so as to be both above and below the vertex's axis.

2. The baffle of claim 1 wherein each vertex and planar surface at vertically opposite angles comprise a set, and wherein there is a vertex for each set of parallel surfaces.

3. The baffle of claim 1 further comprising a clip that supports a tubular UV lamp wherein the clip is affixed to the central post.

4. The apparatus and baffle of claim 1 further comprising baffles oriented in more than one direction around a cross section of a tubular UV lamp.

5. The apparatus of claim 1, wherein the UVC light source is a tubular low-pressure mercury lamp with an emission primarily at 254 nm.

6. The apparatus of claim 1, wherein the UVC light source is a light emitting diode tuned to emit light at 240-285 nm.

7. The apparatus of claim 1, wherein the UVC light source is a light emitting diode tuned to emit light at 265 nm±10 nm.

* * * * *